United States Patent [19]

Sisto et al.

[11] Patent Number: 4,713,367
[45] Date of Patent: Dec. 15, 1987

[54] RETRO-INVERSO ANALOGS OF THE BRADYKININ POTENTIATING PEPTIDE BPP$_{5a}$

[75] Inventors: Alessandro Sisto, Rome; Antonio S. Verdini, Monterotondo; Antonino Virdia, Rome, all of Italy

[73] Assignee: Enichem S.p.A., Milan, Italy

[21] Appl. No.: 821,449

[22] Filed: Jan. 22, 1986

[51] Int. Cl.$^4$ .................... A61K 37/42; C07K 7/18; C07K 7/02

[52] U.S. Cl. .................... 514/17; 530/314; 530/323

[58] Field of Search .................. 530/314, 323; 514/17

[56] References Cited

U.S. PATENT DOCUMENTS 4,522,752 6/1985 Sisto et al. .................... 530/314

Primary Examiner—Delbert R. Phillips

Attorney, Agent, or Firm—Hedman, Gibson, Costigan & Hoare

[57] ABSTRACT

New partially retro-inverso peptides of the following general formula

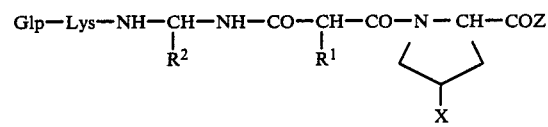

wherein $R^1$ and $R^2$ are the same or different and represent, each independently, the side chain of the aminoacid residues present in the naturally occuring peptides, X is —S—Ph or —O—CH$_2$—Ph and Z is a hydroxy, alkoxy or amino group, are described as well as a suitable method for their preparation. The new compounds are useful as antihypertensive agents.

7 Claims, No Drawings

RETRO-INVERSO ANALOGS OF THE BRADYKININ POTENTIATING PEPTIDE BPP$_{5a}$

The present invention refers to new partially retro-inverso peptide derivatives which are analogues to the bradykinin potentiating peptide (BPP$_{5a}$), useful an antihypertensive agents.

More particularly the present invention relates to new partially retro-inverso peptides of the following general formula

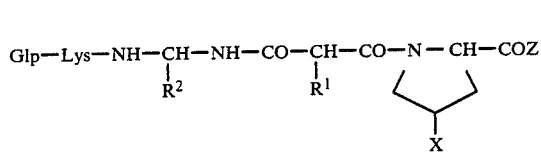

(I)

wherein $R^1$ and $R^2$ are the same or different and represent, each independently, the side chain of the amino acid residues present in the naturally occurring peptides, X is

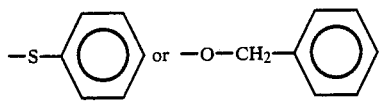

and Z is a hydroxy, alkoxy or amino group, and the pharmaceutically acceptable salts thereof.

Pharmaceutically acceptable salts are salts of the compounds of formula I with various organic and inorganic acids and bases. Such salts, which may conveniently be prepared by conventional methods such as by reacting the free acid or free base forms of the product with one or more equivalents of the appropriate base or acid in a solvent or medium wherein the salt is insoluble or in a solvent which is then easily removed, include ammonium salts, alkali metal and alkaline earth metal salts such as sodium, potassium, calcium and magnesium salts, salts with organic bases e.g. N-methyl-D-glucamine and dicyclohexylamine, salts with basic amino acids e.g. arginine and lysine, and the like; also salts with organic or inorganic acids such as HCl, HBr, H$_2$SO$_4$, H$_3$PO$_4$, sulphonic acids, oxalic acid, acetic acid, pivalic acid and the like.

While the non-toxic physiologically acceptable salts are preferred, other salts may also be useful e.g. in isolating or purifying the product.

A preferred group of compounds of the present invention comprises those compounds of formula (I) wherein $R^1$ is selected from the group consisting of methyl, 2-propyl, 2-butyl, and 2-methyl-1-propyl corresponding to the side chains of alanine, valine, isoleucine and leucine and $R^2$ is selected from the group consisting of benzyl, 4-hydroxy-benzyl, and 4-imidazolylmethyl, corresponding to the side chains of phenylalanine, tyrosine and histidine respectively, X is as defined above and Z is hydroxy or alkoxy.

A most preferred group comprises those compounds of formula I wherein $R^1$ is methyl, corresponding to the side chain of alanine, $R^2$ is benzyl, corresponding to the side chain of phenylalanine, X is as defined above and Z is hydroxy.

The compounds of the present invention which inhibit the angiotensin converting enzyme in vitro, are useful as antihypertensive agents.

Over the past decade, in fact, a mass of data has accumulated supporting a major role for the renin-angiotensin-aldosterone system in determining the onset of hypertension. It is now clear that the action of renin on a pseudoglobulin of blood plasma produces the decapeptide angiotensin I, which is quickly converted to the active pressor agent, the octapeptide angiotensin II. Angiotensin II, besides exerting a powerful vasoconstricting action on the arterial smooth muscle, acts directly on the adrenal gland to stimulate aldosterone secretion which in turn produces sodium retention.

Conversion of angiotensin I to angiotensin II is brought about by the angiotensin converting enzyme (ACE) which is also responsible for inactivating bradykinin, a nonapeptide with powerful hypotensive action.

The net result of this dual action by the angiotensin converting enzyme is an increase in arterial blood pressure. Recently, peptides which potentiate bradykinin activity, have been isolated from some low molecular weight fractions extracted from the venom of the Bothrops Jararaca snake.

Further studies have shown that these peptides are also active as ACE inhibitors.

Among these peptides, the pentapeptide Glp-Lys-Trp-Ala-Pro (BPP$_{5a}$) has been found to be the most potent ACE inihibitor. The interest of such inhibitors resides in the possibility of reducing or controlling the angiotensin related hypertension due to the conversion of angiotensin I into angiotensin II by the angiotensin converting enzyme or kinase II in mammals. Compounds which inhibit the angiotensin converting enzyme may be useful as antihypertensive agents in the treatment of renal hypertension, malignant hypertension and essential hypertension.

These inhibitors are also useful as diagnostics.

In fact, in the long-term treatment of hypertension, the possibility of determining the degree of involvement of the renin-angiotensin system by the use of ACE inhibitors, would be of great importance in choosing the therapeutic treatment. The pentapeptide BPP$_{5a}$ appears to be potentially effective in therapy as it is capable of controlling the reno-vascular hypertension induced experimentally in rats, potentiates the in vivo activity of bradykinin injected directly into the coronary arteries and, when infused directly into the brain, inhibits the CNS-mediated hypertensive and tackycardic action of angiotensin I.

However, as also the in vivo biological stability is an essential requirement for the use of peptide inhibitors as drugs, the extreme lability of BPP$_{5a}$ to the angiotensin converting enzyme has prejudiced its use in pharmacology. Ondetti M. A. et al. (Annular Reports in Medicinal Chemistry, Chap. 9, 88, 1978) reports in fact a complete loss of inhibitory activity after 15 minutes of preincubation of BPP$_{5a}$ with the angiotensin converting enzyme.

According to Italian patent application 24369 A/82, BPP$_{5a}$ analogs resistant to the action of the enzyme are synthetized by replacing the tryptophan moiety with phenylalanine and suitably inverting the Phe$^3$-Ala$^4$ bond of the peptide sequence which showed to be the most susceptible one to enzymatic hydrolysis.

The obtained compound, i.e. the pentapeptide Glp-Lys-gPhe-mAla-Pro-OH, when tested in vitro in the inhibition of the angiotensin converting enzyme, gave an IC$_{50}$ more than 1000 times higher than that of the natural product (BPP$_{5a}$) or the corresponding uninverted peptide Glp-Lys-Phe-Ala-Pro-OH.

It has now been found that by replacing the proline residue in the retro-inverso peptide sequence with a proline residue C-substituted with a

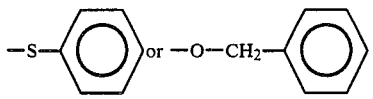

group, the ACE inhibitory activity of the obtained compounds is very high (only 10 times lower than that of the natural product) while their stability in the presence of the enzyme is quite remarkable.

In particular, comparative experiments carried out in vivo in order to evaluate the ACE inhibitory activity of the compounds of the present invention gave the results reported in following table I (IC$_{50}$ represents the concentration of the test compound, in $\mu M$, which inhibits the angiotensin converting enzyme by 50%. The enzyme employed in this test has been isolated from rabbit lungs according to the method by Cushman and Cheung described in Biochem. Pharmacol. 20, 1637, (1971)).

TABLE I

| Peptide sequence | IC$_{50}$ ($\mu M$) |
| --- | --- |
| (a) Glp—Lys—gPhe—(S)mAla—Pro(S—Ph)—OH | 1.1 |
| (b) Glp—Lys—gPhe—(R)mAla—Pro(S—Ph)—OH | 70 |
| (c) Glp—Lys—Phe—Ala—Pro—OH | 0.1 |
| (d) Glp—Lys—Trp—Ala—Pro—OH (BPP$_{5a}$) | 0.1 |
| (e) Glp—Lys—Phe—Ala—Pro(S—Ph)—OH | 0.06 |
| (f) Glp—Lys—gPhe—(S)mAla—Pro—OH | 140 |
| (g) Glp—Lys—gPhe—(R)mAla—Pro—OH | 290 |

While compounds (c), (d) and (e) are quickly degraded, in vitro, by the angiotensin converting enzyme, compounds (a), (b), (f) and (g) display complete resistance towards cleavage by ACE.

In vivo experiments carried out in anesthetized normotensive rats confirmed a hypotensive effect of the compounds of the invention as compound (a), when injected intravenously at a dosage of 0.18 mg/Kg, produced a blood pressure decrease of about 20 mmHg.

The compounds of the present invention are therefore useful in treating hypertension and other related clinical conditions. To this purpose the compounds of this invention may be utilized in solid or liquid dosage forms such as tablets, capsules or elixirs for oral administration, or sterile solutions or suspensions for intravenous or intramuscular administration.

It is apparent to any skilled person that the daily dosage to be administered to patients in need of such treatment to provide optimal pharmaceutical efficacy will vary from patient to patient depending upon the nature and severity of the disease, the patient's weight, the route of administration and other possible concurrent medical treatments.

However, a suitable daily dosage will generally be about 1 to 1000 mg, preferably administered in 2 or 3 subdivided doses. Preferably, a dosage range will be about 2.5 to 250 mg and more preferably about 2.5 to 100 mg per day per patient.

The compounds of the present invention can also be administered in combination with other antihypertensive agents known in the art or currently used in therapy. Typically, the compounds of the invention can be formulated into pharmaceutical compositions containing the active ingredient of formula I or a physiologically acceptable salt thereof, and, optionally, additional antihypertesively active ingredients, compounded with a physiologically acceptable vehicle, carrier, excipient, binder, preservative, stabilizer, flavoring agent etc. in a unit dosage form as called for by accepted pharmaceutical practice. The amount of active principle in these compositions is such that a suitable dosage in the range indicated above is obtained.

The compounds of formula I are readily prepared through condensation of a N-monoacylated gem-diamino residue of the formula

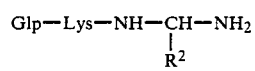

wherein $R^2$ is as defined above and the functional groups are suitably protected, with a peptide fragment of the formula

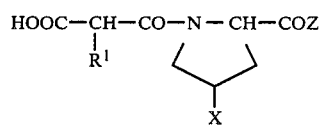

wherein $R^1$ and X are as defined above, and the functional groups, if any, are suitably protected, and Z is an easily removable alkoxy group, in the presence of N,N'-dicyclohexylcarbodiimide or N-hydroxy-benzotriazole as the coupling agent.

The condensation reaction is typically carried out by contacting about equimolar proportions of the reaction partners and the coupling agent at a temperature comprised between $-10°$ C. and room temperature, in the presence of a highly polar, aprotic organic solvent. Suitable solvents are for instance di-methylformamide, dimethyl sulfoxide and the like solvents.

Preferably the condensation is carried out by slowly adding a solution of an acid addition salt of the compound of formula II wherein $R^2$ is as defined above and the functional group, if any, of the radical $R^2$, as well as the lysine amino group are suitably protected, in the presence of an acid accepting agent such as a tertiary amine, to a solution of the reactant of formula III and the coupling agent.

Once the condensation is over, the temporary protecting groups are removed and the obtained peptide of formula I is recovered and purified, for istance, by extraction, counter-current distribution, precipitation, crystallization or chromatographic methods.

In compounds of general formula I, the carbon atom to which $R^1$ is attached may have the L- or D-configuration while all the other amino acid moieties of the sequence have the L-configuration. The compounds accordingly exist in two isomeric forms or in mixtures thereof. If a reactant of formula III having a fixed configuration at the -C-$R^1$ atom is used in the above process, only one isomer of the compounds of formula I is selectively obtained. Alternatively, if desired, when a mixture of isomers is obtained, it can be separated by conventional chromatographic methods, typically reverse-phase HPLC, into the single pure isomers.

Although the amino acid partial structure

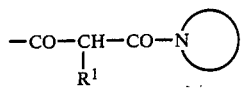

in the sequence of formula I, is generally preferred in the L- (or S-) configuration, the compounds of formula I can be employed as pure L- (or S-) isomeric compounds or in a mixture of S- and R-isomers as this last one, which is by far less active than the S-isomer, is however not toxic.

Typically, purification as well as separation into the single isomers, can be achieved by reverse-phase HPLC, using a Lichroprep 25-40 μm resin (Merck) as the stationary phase and eluting with a CH$_3$CN/H$_2$O mixture containing 0.1% trifluoroacetic acid.

Product identity is confirmed by NMR.

Product purity is checked by reverse-phase HPLC (RP-HPLC) using the following eluting systems: H$_2$O/-MeCN, TFA 0.1% in aqueous/MeCN solution and by silica gel tlc using the following eluting systems: n-butanol/acetic acid/water (4/1/1); chloroform/methanol/acetic acid (85/10/5); n-butanol/isopropanol/1N NH$_4$OH/ethyl acetate (1/1/5/1), organic phase.

The starting compounds of formulas II and III may be prepared easily according to known techniques such as for instance the peptide synthesis method described by Bodonszki M. and Ondetti M. A. in Peptide Synthesis, Interscience, N.Y., 1976; and The Peptides, Vol. 1, Gross E. and Meienhofer L. Ed., Academic Press, New York, 1979.

The following example further illustrates preparation of a representative compound of the present invention and of the starting compounds of formulas II and III.

The following abbreviations are used throughout the present specification:

Boc=tert-butoxycarbonyl; Z=benzyloxycarbonyl; EtO=ethyl ester; OBu$^t$=tert-butylester; DCC=N,N'-dicyclohexylcarbodiimide; DCU=dicyclohexylurea; HOBt=N-hydroxy-benzotriazole; DMF=N,N-dimethylformamide, THF=tetrahydrofuran; NMM=N-methylmorpholine, MeOH=methanol; EtOH=ethanol; MeCN=acetonitrile; EtOAc=ethyl acetate; Et$_2$O=ethyl ether; TFA=trifluoroacetic acid; BTI=1,1[bis(trifluoroacetoxy)iodo]benzene.

EXAMPLE 1

Synthesis of Pyroglutamyl-lysyl-gemphenylalanyl-(R,S)(2-methylmalonyl)-(4-allo-thiophenyl)(proline)

Synthesis of N$^\alpha$-tertbutoxycarbonyl-phenylalanylamide
Boc-PheNH$_2$

BocPhe (2.65 g, 10 mmol) is dissolved in anhydrous THF (15 ml).

NMM (1.01 g, 10 mmol) and isobutylchloroformate (1.36 g, 10 mmol) are added to the obtained solution, cooled to −15° C. and kept under nitrogen atmosphere, and, 2 minutes later, a 28% aqueous ammonium hydroxide (0.375 g, 11 mmol) solution is added thereto.

During the additions the temperature is kept lower than −10° C.

After 2 hours, the solvent is evaporated off and the residue is precipitated by the addition of excess water.

The obtained product is filtered, washed with water and then dried over P$_2$O$_5$.

M.p.=147°-148° C.;
[α]$_D^{25}$=0.54° (c=3.0 in DMF)

Elemental analysis: calculated for C$_{14}$H$_{20}$N$_2$O$_3$: %C 63.61; %H 7.63; %N 10.60; found %C 63.50; %H 7.70; %N 10.61.

Chromatographic analysis (tlc and HPLC) shows no impurities while the $^1$H NMR confirms the assigned structure.

Synthesis of N-Benzyloxycarbonyl-Lysyl(N$^\epsilon$-tert-butoxycarbonyl)phenylalanylamide:
Z-lys-(Boc)-PheNH$_2$Z-lys(Boc)(1.9 g, 5 mmol) is dissolved in anhydrous THF (15 ml).

NMM (0.5 g, 5 mmol) and isobutylchloroformate (0.68 g, 5 mmol) are added to the obtained solution cooled to −15° C. and kept under nitrogen atmosphere.

Two minutes later, a solution of PheNH$_2$HCl (1.2 g, 0.6 mmol), obtained by cleavage of the t-butoxycarbonyl group from BocPheNH$_2$ with 4.5N HCl in EtOAc, and NMM (0.6 g, 6 mmoles) in DMF is added thereto.

The temperature, during the additions, is kept lower than −10° C. Once the disappearance of PheNH$_2$ has been checked, the reaction mixture is concentrated to dryness. The residue, taken up in EtOAc, is washed with 5% sodium bicarbonate, water, 5% citric acid, and water.

The EtOAc solution is dried over MgSO$_4$ and the product obtained by evaporating off the solvent is washed with Et$_2$O and then dried.

M.p.=182°-184° C.
[α]$_D^{21}$−20.8° (c=1.0 in DMF)

Elemental analysis: Calculated for C$_{28}$H$_{30}$N$_4$O$_6$: %C 63.86; %H. 7.27; %N 10.64; Found: %C 63.77; %H 7.0; %N 10.59;

Synthesis of pyroglutamyl-lysyl(N$^\epsilon$-tertbutoxycarbonyl)phenylalanylamide:
Glp-Lys(Boc)-PheNH$_2$Glp (0.516 g, 4 mmol) is dissolved in anhydrous THF (20 ml).

NMM (0.4 g, 4 mmol) and isobutylchloroformate (0.53 g, 4 mmol) are added to the obtained solution, cooled to −15° C. and kept under nitrogen atmosphere and, two minutes later, a DMF solution of Lys(Boc)-PheNH$_2$ (1.6 g, 4 mmol), obtained by cleavage of the benzyloxycarbonyl group from Z-Lys(Boc)-PheNH$_2$ through catalytic hydrogenation over 10% Pd-on-carbon, is added.

During the reaction the temperature is maintained lower than −10° C. Once the disappearance of Lys(-Boc)-PheNH$_2$ has been checked, the solvent is evaporated off to dryness and the residue is washed with 5% NaHCO$_3$, water, 5% citric acid, and water. After drying over P$_2$O$_5$, the product is washed with Et$_2$O and then dried again.

M.p.=180°-82° C.
[α]$_D^{21}$=−19.68° (c=0.56 in DMF/hexafluoroisopropanol 1/1 v/v)

Elemental analysis: calculated for C$_{25}$H$_{37}$N$_5$O$_6$: %C 59.62; %H 7.41; %N 13.91; found %C 59.59; %H 7.32; %N 13.85.

Synthesis of t-butoxycarbonyl-L-(4-allo-thiophenyl)-proline
Boc-Pro(4-allo-S-Ph)OH Boc-Pro(4-allo-S-Ph)-OMe (3.59 g, 10.6 mmol) is dissolved in methanol (10 ml) at a temprature of about 4° C.

A solution of NaOH (1.27 g, 31.8 mmol) in methanol (10 ml) is added to the obtained solution. The hydrolysis is carried out at a temperature of 4° C. for 16 hours. At the end of the reaction, the reaction mixture is diluted with water, methanol is evaporated off and the aqueous phase is neutralized with 0.1N HCl.

The aqueous solution is extracted with ethyl acetate, the organic solvent is evaporated off and the raw product thus obtained is purified by silica gel absorption chromatography (Lobar-Merck) eluting with a mixture n-hexane/ethyl acetate 80/20 (v/v).

An oily product (3.37 g, 94%) is thus obtained.

Elemental analysis Calculated for $C_{16}H_{21}NO_4S$: %C 49.4; %H 6.49%; %N 3.10%; found %C 48.0; %H 6.40; %N 2.86

Synthesis of L-(4-allo-thiophenyl)proline hydrochloride

L-(4-allo-S-Ph)proline-OH-HCl

Boc-(4-allo-SPh)Pro-OH (3.23 g, 10 mmol) is dissolved in ethyl acetate (20 ml) saturated with HCl, and the obtained solution is kept at room temperature (20°–25° C.) for 15 minutes.

Then the solvent is evaporated off and a powdered product (2.5 g) is recovered with m.p.=138°–140° C.

$^1$H-NMR analysis confirms the product purity.

Synthesis of (4-allo-thiophenyl)proline t-butyl ester dibenzensulfonimide salt:

DBSI.H-Pro(4-allo-S-Ph)OBu$^t$HCl.HPro(4-allo-S-Ph)-OH (2.59 g, 10 mmol) is dissolved in a mixture dioxane/ethylene glycol 9/1 (v/v) (25 ml).

The solution, kept at a temperature of about 4° C., is saturated with isobutylene and stirred at room temperature for 48 hours. At the end of the reaction, the mixture is treated with aqueous 5% NaHCO$_3$ and then extracted with ethyl acetate.

The solvent is evaporated off to dryness and the oily residue is taken up in ethyl acetate and dried over MgSO$_4$.

After filtering off the salt and adding dibenzensulfonimide, the reation mixture is evaporated to dryness and the desired product is recovered as a crystalline product from ethyl ether/petroleum ether 40/60 (v/v) (4.4 g).

M.p. 98°–99° C. and $[\alpha]_D^{25} -7.2°$ (c=0.5 in MeOH)

Synthesis of (R,S)-2-methylmalonyl-(4-allo-thiophenyl)proline tert-butyl ester

EtOOC-CH(CH$_3$)-CO-Pro(4-allo-S-Ph)-OBu$^t$EtOOC-CH(CH$_3$)-COOH (0.297 g, 2.1 mmol) and HOBt (0.297 g, 2.1 mmol) are added to a CH$_2$Cl$_2$ (20 ml) solution of H-Pro(4-allo-S-Ph)-OBu$^t$ (0.45 g, 1.6 mmol) obtained by treatment of DBSI.H-Pro(4-allo-S-Ph)-OBu$^t$ in ethyl acetate with aqueous 5% NaHCO$_3$, and after cooling the reaction mixture to about 0° C., DCC (0.429, 2.1 mmol) is added thereto.

The reaction mixture is stirred at room temperature for about 120 minutes.

Dicyclohexylurea which precipitates is removed by filtration and the obtained mixture is washed with aqueous 5% NaHCO$_3$, 5% citric acid, and a saturated NaCl aqueous solution.

The raw product thus obtained is dissolved into ethyl acetate and then dried over MgSO$_4$.

The product is purified by silica gel absorption chromatography, eluting with n-hexane/ethyl acetate 70/30 (v/v). An analytically pure oily product (0.23 g, 37.5%) is thus obtained.

Synthesis of (R,S)-2-methylmalonyl-(4-allo-thiophenyl)proline tertbutyl ester

EtOOC-CH(CH$_3$)-CO-Pro(4-allo-S-Ph)-OBu$^t$ (0.230 g, 0.6 mmol) is dissolved in methanol (1.5 ml) containing 0.072 g of NaOH and the reaction is allowed to proceed for 15 minutes. Water is then added, methanol is evaporated off, the aqueous solution is acidified by the addition of citric acid to pH 4.0, and extracted with ethyl acetate.

The organic solution is then washed with a saturated NaCl aqueous soluton and dried over MgSO$_4$.

After filtering off the salt, the organic solvent is evaporated off under vacuum yielding 0.182 g (80%) of an oily product.

The $^1$H-NMR spectrum confirms the assigned structure and the chromatographic analyses (tlc and HPLC) confirm the purity of the product.

Synthesis of pyroglutamyl-lysyl(N$^\epsilon$-tert-butoxycarbonyl) gemdiaminophenylalanyl-(R,S)2-methylmalonyl-(4-allo-thiophenyl)proline tert-butyl ester Glp-Lys(Boc)-gPhe-(R,S)mAla(4-allo-S-Ph)proline-OBu$^t$.

HOOC-CH(CH$_3$)-CO-Pro(4-allo-S-Ph)OBu$^t$ (0.182 g, 0.48 mmol) is dissolved in DMF (10 ml).

HOB$^t$ (0.068 g, 0.48 mmol) and DCC (0.099 g, 0.48 mmol) dissolved in DMF, are then added to the obtained solution, cooled to 0° C. After 20 minutes Glp-Lys(Boc)-gPhe-H.HCl (0.200 g, 0.4 mmol) dissolved in a solution of DMF and triethylamine (66 μl, 0.4 mmol) is added thereto.

The reaction mixture is allowed to stand at 0° C. for 1 hour and then at room temperature overnight.

The DCU which precipitates is removed by filtration and washed carefully with cold DMF (4° C.). The remaining solution and the washing solvent are combined and concentrated to dryness.

The obtained product is thoroughly triturated with ethyl acetate and sequentially washed with aqueous 5% NaHCO$_3$, 5% citric acid and saturated NaCl aqueous solution.

The product is then triturated again with ethyl acetate yielding 0.200 g (58%) of a pure product with m.p.=140°–142° C.

$[\alpha]_D^{25} = -18.0°$ (c=1 in MeOH)

Chromatographic analysis shows no trace of impurities and $^1$H-NMR analysis confirms the assigned structure.

Synthesis of pyroglutamyl-Lysyl(N$^\epsilon$-hydrochloride)-gemdiaminophenylalanyl-(R,S)-2-methylmalonyl-(4-allo-thiophenyl)proline Glp-Lys(HCl)-gPhe-(R,S)mAla-Pro-(4-allo-S-Ph)-OH Hydrogen chloride is bubbled for 10 minutes into a suspension of Glp-Lys(Boc)-gPhe-(R,S)mAla-Pro(4-allo-SPh)OBu$^t$ (0.08 g, 0.1 mmol) in methylene chloride (10 ml).

After having checked the disappearance of the starting product, the solvent is evaporated off to dryness, the residue is taken up in a mixture H$_2$O/TFA 90.10 (v/v) and the precipitate is removed by filtration.

The obtained solution is evaporated to dryness and the desired product is isolated by reverse-phase preparative HPLC with 35 g of Lichroprep 25–40 μm (Merck) as the stationary phase and eluting with a 15% H$_2$O/MeCN mixture containing 0.1% TFA.

The fractions containing the desired product are collected and MeCN is evaporated off.

The desired product is then freeze-dried.

$[\alpha]_D^{25} = -15°$ (c>1 in MeOH).

Amino acid analysis: 1 Glu (1.07); 1 Lys (0.92).

We claim:

1. A peptide of the general formula

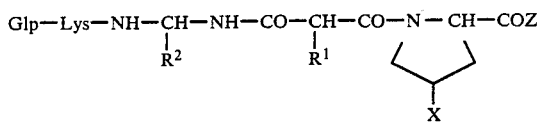 (I)

wherein R² and R¹ are the same or different and represent, each independently, the side chain of an aminoacid residue present in the naturally occuring peptides, X represents -S-Ph or -O-CH₂-Ph, and Z is a hydroxy, alkoxy or amino group; and pharmaceutically acceptable salts thereof.

2. A peptide according to claim 1 wherein R¹ is selected from the group consisting of methyl, 2-propyl, 2-butyl, and 2-methyl-1-propyl, R² is selected from the group consisting of benzyl, 4-hydroxybenzyl, and 4-imidazolylmethyl, and Z is hydroxy or alkoxy.

3. A peptide as in claim 2 wherein R¹ is methyl, R² is benzyl and Z is hydroxy.

4. A peptide as in claim 3 which is Glp-Lys-gPhe-mAla-Pro(4-allo-S-phenyl)-OH.

5. A peptide as in claim 4 which is Glp-Lys-gPhe-m(S)Ala-Pro(4-allo-S-phenyl)-OH.

6. A pharmaceutical composition comprising an antihypertensive effective amount of the peptides of claims 1, 2, 3, 4 or 5 alone or in combination with a pharmaceutically acceptable carrier.

7. A method of inducing an antihypertensive effect in a warm-blooded animal comprising administering to said warm-blooded animal the pharmaceutical composition of claim 6.

* * * * *